(12) United States Patent
Meier et al.

(10) Patent No.: US 6,987,867 B1
(45) Date of Patent: Jan. 17, 2006

(54) PROCESS FOR EVALUATING DATA FROM TEXTILE FABRICS

(75) Inventors: Rudolf Meier, Uster (CH); Jürg Uhlmann, Frauenfeld (CH)

(73) Assignee: Uster Technologies AG, Uster (CH)

(*) Notice: Subject to any disclaimer, the term of this patent is extended or adjusted under 35 U.S.C. 154(b) by 0 days.

(21) Appl. No.: 09/508,430

(22) PCT Filed: Aug. 14, 1998

(86) PCT No.: PCT/CH98/00343

§ 371 (c)(1),
(2), (4) Date: Mar. 13, 2000

(87) PCT Pub. No.: WO99/14580

PCT Pub. Date: Mar. 25, 1999

(30) Foreign Application Priority Data

Sep. 15, 1997 (CH) .................... 2167/97

(51) Int. Cl.
*G06K 9/00* (2006.01)

(52) U.S. Cl. .................................... 382/111
(58) Field of Classification Search ............ 382/111
See application file for complete search history.

(56) References Cited

U.S. PATENT DOCUMENTS

| | | | |
|---|---|---|---|
| 3,613,743 A * | 10/1971 | Sakamoto | 250/559.42 |
| 4,728,800 A * | 3/1988 | Surka | 382/149 |
| 4,745,555 A * | 5/1988 | Connelly et al. | 700/130 |
| 5,544,256 A | 8/1996 | Brecher et al. | 382/149 |
| 5,745,365 A * | 4/1998 | Parker | 700/122 |
| 5,834,639 A * | 11/1998 | Meier et al. | 73/159 |
| 6,100,989 A * | 8/2000 | Leuenberger | 356/430 |
| 6,501,086 B1 * | 12/2002 | Leuenberger | 250/559.45 |
| 2002/0062775 A1 * | 5/2002 | Hoeller | 112/285 |

FOREIGN PATENT DOCUMENTS

| | | |
|---|---|---|
| DE | 36 39 636 | 5/1988 |
| EP | 0491954 A1 | 1/1992 |
| EP | 0 491 954 | 7/1992 |
| FR | 2 701 766 | 8/1994 |
| GB | 2 253 697 | 9/1992 |

OTHER PUBLICATIONS

B. Nickolay, et al., "Automatic Textile Inspection", Studie fur die Textilindustrie, 60 pages, Jun. 1993.
E. Ersö, et al., "Rationelle 100% Optische Kontrolle in Der Vlies—Und Textilstoffproduktion", ISRA Systemtechnik GmbH, 16 pages.
Ferdinand van der Heijden, "Statistical Patter Classification and Parameter Estimation", Image Based Measurement Systems, Object Recognition and Parameter Estimation, John Wiley & Sons, 1994.

* cited by examiner

*Primary Examiner*—Andrew W. Johns
*Assistant Examiner*—Shervin Nakhjavan
(74) *Attorney, Agent, or Firm*—Buchanan Ingersoll PC

(57) ABSTRACT

A process is disclosed for evaluating data obtained from textile fabrics. In order to devise a process which allows data obtained from textile fabrics to be easily compared, assessed in a differentiated manner as to their significance and evaluated, the data are determined in a section (3*a*,3*b*) of the surface of the fabric, sorted according to at least two parameters (13,14) and represented in an image (12, 30) as a function of the parameters.

17 Claims, 6 Drawing Sheets

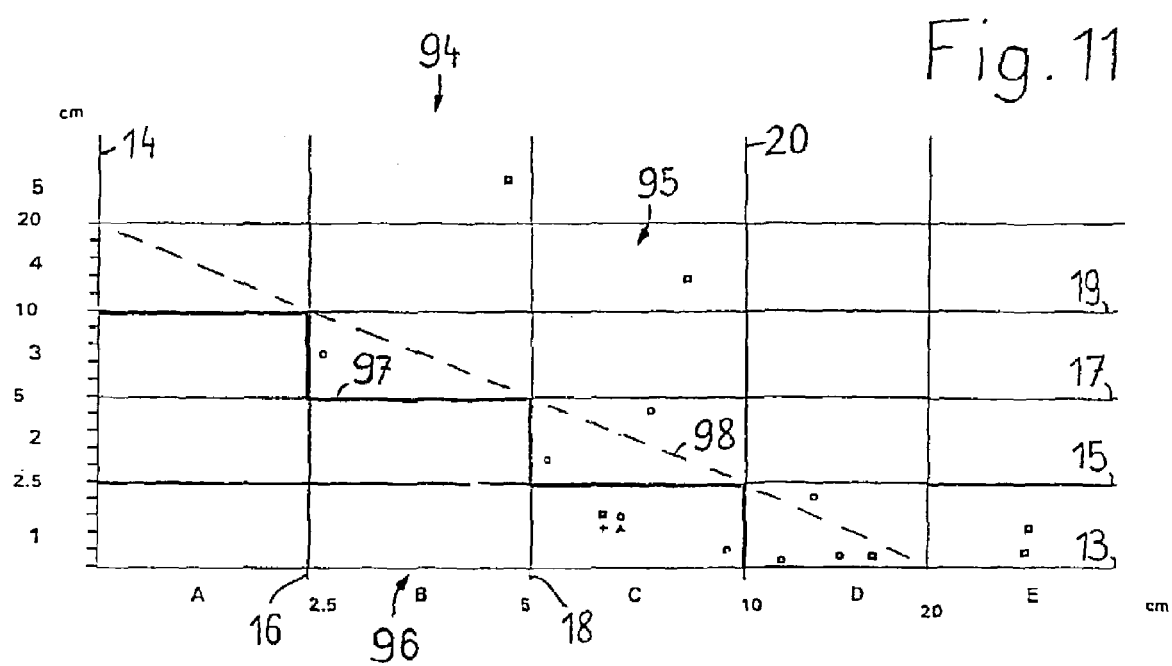

PROCESS FOR EVALUATING DATA FROM TEXTILE FABRICS

FIELD OF THE INVENTION

The invention relates to a method for evaluating data determined on textile fabrics.

BACKGROUND OF THE INVENTION

When producing textile fabrics such as woven fabrics, knitted fabrics, etc., faults which cause the ideally regular and precisely structured surface to exhibit irregularities or faults are a frequent occurrence. In terms of extent, faults of this kind may range from being very small and inconspicuous to very large or, for other reasons, conspicuous and may reduce the value and the function, e.g. the strength or the appearance of the fabric. The finished fabrics are therefore subjected to an examination for the purpose of indicating faults in the structure. This may be a visual or a machine examination and often takes place both before dyeing or dressing and also before making up. An increase in the quantity of detected faults is to be expected in particular when carrying out a machine or automated examination, so that a correspondingly greater data flow may result.

One disadvantage in this case lies in the fact that, although a considerable amount of data is available, these data are likely to cause confusion and may not just serve to improve the quality of the products. It should also be borne in mind that there are a great many producers of textile fabrics of all kinds and that each producer and also many customers are inclined to define and implement their own quality criteria. This means that textile fabrics which are assessed by different individuals or institutions result in assessments which cannot easily be compared with one another.

SUMMARY OF THE INVENTION

As characterized in the claims, the invention therefore achieves the object of providing a method by which faults which are determined in textile fabrics can easily be compared with one another and assessed and evaluated as to their significance in a differentiated manner.

This is achieved by determining the data on a swatch of the surface of the fabric and sorting this data according to at least two parameters. A swatch can be understood to be the entire surface under consideration of a fabric or a section from the surface. A section of this kind may be moved or changed after a period required for acquiring the data, so that new data on other zones or swatches of the fabric are periodically obtained. The intensity of a pixel or surface element, a longitudinal coordinate, a latitudinal coordinate, etc. may be considered as data and therefore also as parameters, for example. The acquired data on the faults are then represented in an image as a function of selected parameters, which in turn may be divided into zones which in themselves are conceived as homogeneous. If two parameters are selected, the result is a one-dimensional representation. If three parameters are selected, the resulting image is a two-dimensional representation. The image then represents, for example, a classifying field consisting of individual fields which define a class. The class is characterized by the extent of the field, which lies in a plane which is regarded as the location for values of two parameters. A further parameter may be displayed by symbols entered in the field.

The advantages achieved by means of the invention lie in particular in the fact that it enables a structured and standardized assessment of faults in textile fabrics to be carried out. Thus on the one hand values of predetermined parameters for the most varied faults can be indicated, while on the other criteria can be created which help to identify the significance or value of the faults and to compare this with the value of other faults. A large data flow on faults in the fabrics can thus also be processed to provide accurate information on the faults occurring.

BRIEF DESCRIPTION OF THE DRAWINGS

The invention is illustrated in detail in the following on the basis of an example and with reference to the accompanying figures, in which:

FIGS. 3 to 11 in each case show a classifying field.

DETAILED DESCRIPTION

Figure 1:
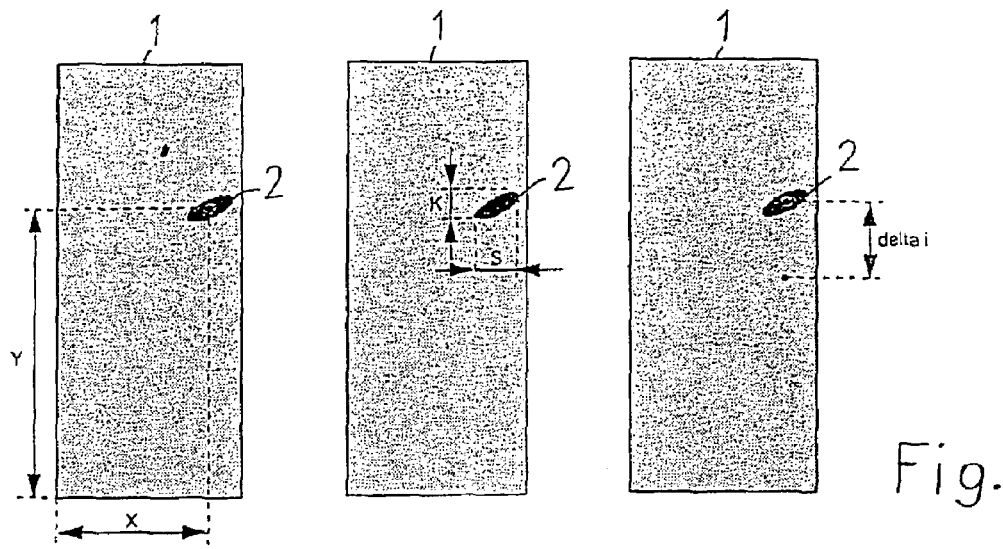
FIG. 1 shows a respective swatch of the surface of a textile fabric.

FIG. 1 shows the same run 1 of a textile fabric three times with a fault 2. Information on the position of this fault 2 can be obtained, for example, via coordinates x and y, on its size via values of the extent in two directions s and k, and on its intensity or deviation, for example in terms of color, from the surrounding area via a value delta i.

Figure 2:
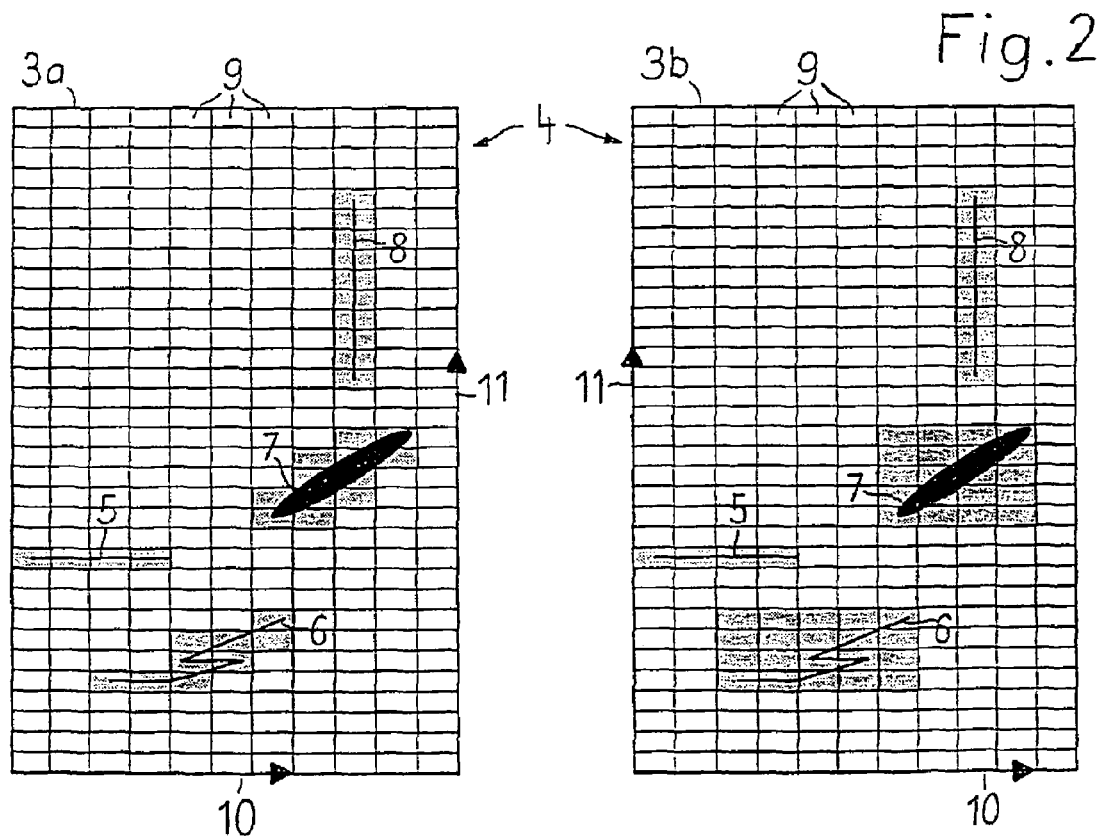
FIG. 2 shows a respective swatch according to FIG. 1 with different faults.

FIG. 2 shows a respective swatch 3a, 3b of a textile fabric with a grid 4 and four different faults 5, 6, 7 and 8. The swatch 3a shows a first possibility for evaluating the size of the faults 5, 6, 7 and 8 and the swatch 3b a second possibility. For this purpose the grid 4 divides the swatches 3a, 3b into individual small fields 9, and the occupancy of these fields by the faults 5–8 is interpreted differently in the two swatches 3a and 3b, as will be discussed further in the following. However in both cases this means that the extent of the faults through the number of occupied fields is selected as a parameter. Although—should this be a woven fabric—the faults 5, 6, 7, 8 extend in two directions, weftwise 10 and warpwise 11, the values of the parameters only indicate that the intensity of the faults 5–8 has exceeded a threshold value and one of the number of occupied fields 9 has a proportional extent. The swatches 3a, 3b preferably form at least one rectangle whose sides extend parallel and perpendicularly to boundaries of the fabric or run 1.

Figure 3:
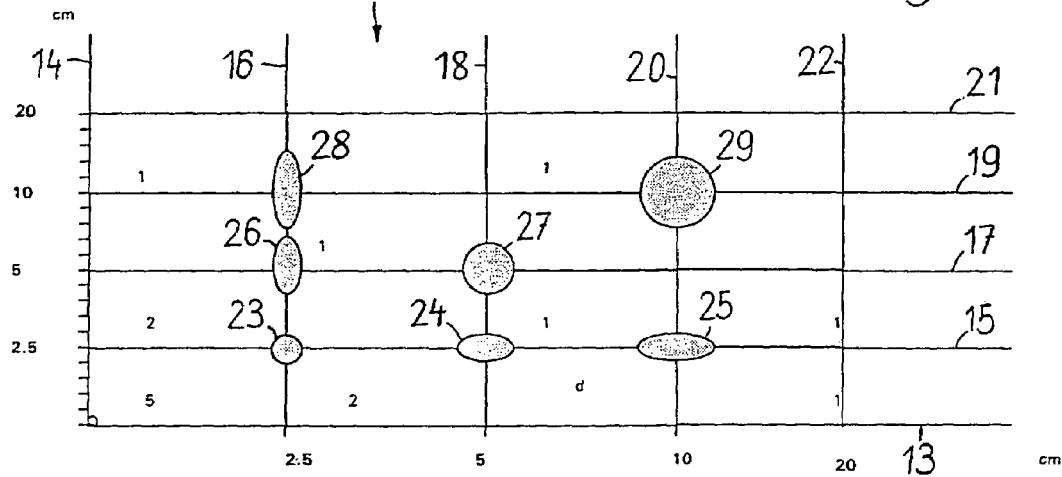

FIG. 3 shows an image 12 with two axes 13, 14, along which values of parameters are plotted. Here the values along the axis 13 are values for the length of a fault, for example viewed weftwise in a woven fabric, and those along the axis 14 values for the width of a fault, for example viewed warpwise in a woven fabric. Lines 15, 17, 19 and 21 divide the width of the faults into five classes, while lines 16, 18, 20 and 22 divide the length of the faults into five classes. This results overall in twenty five classes for classifying the faults according to size. Symbols 23–29 are drawn in at a plurality of class boundaries, which are indicated by the lines 15–22, these symbols representing the form of a fault as is to be expected on the basis of dimensions according to the said lines. Numerical values are also entered in the fields defined by the lines 15 to 22, these values indicating the number of detected faults which fall within the class concerned. For this purpose it is assumed that a class represents a homogeneous zone, i.e. no distinction is made as to whether or not the values of the parameters lie near upper or lower class boundaries or lines 15–22.

Figure 4:
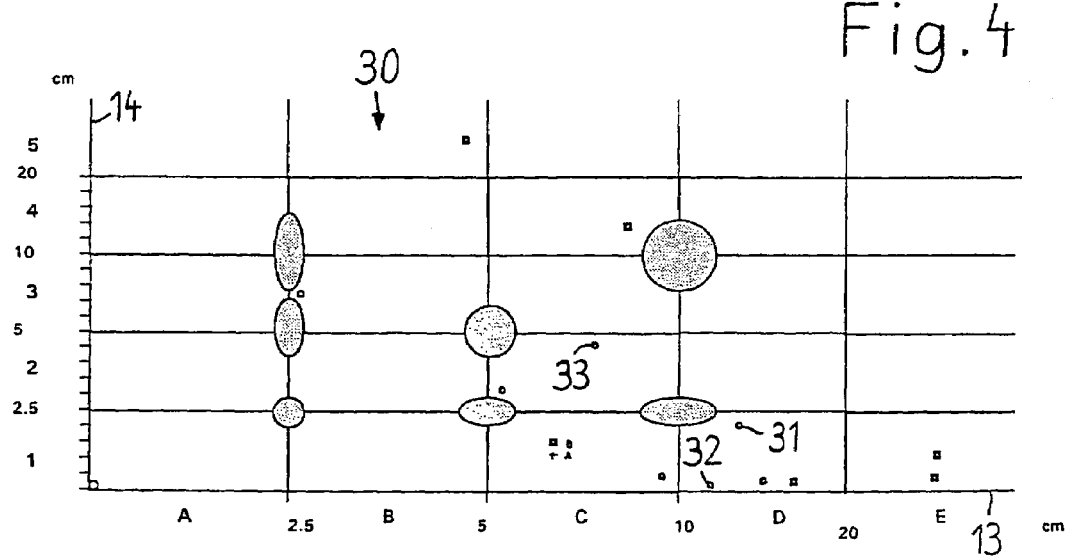
Figure 5:
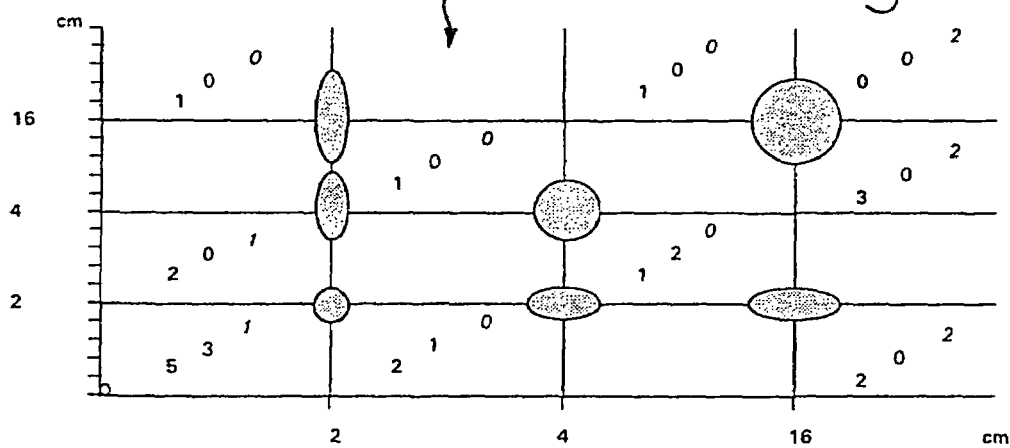
Figure 6:
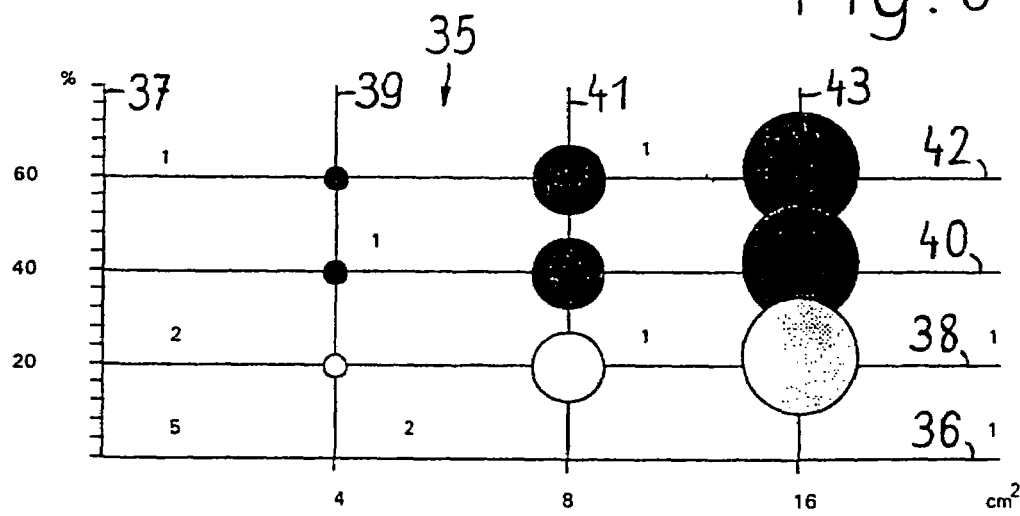

FIG. 4 shows an image 30 with axes and lines defining classes as is already known from FIG. 3. The axes, lines and symbols have therefore been given the same reference numbers. Dots 31, 32, 33, etc. are entered in the fields, the position of which dots in relation to the axes 13 and 14 indicates the size of the fault accurately or in a differentiated manner. Each dot therefore corresponds to a fault, and the distribution of the faults or the dots thereof is also an indication of the predominant type of fault in the fabric. Characters A to E are also entered along the axis 13 between the lines 14 to 22 and integral numbers 1 to 5 along the axis 14 between the lines 13 to 21. Each field and therefore each class can therefore be clearly designated by the combination of a number and a character. FIG. 5 shows an image 34 with axes and lines defining classes as is already known from FIG. 3. The axes, lines and symbols have therefore been given the same reference numbers. Diagonally ascending numerical values, which indicate the intensity of a fault, are provided in the individual fields, which correspond to fault classes. Here the position of a figure indicates the intensity, while the value of the figure indicates the number of faults with this intensity. Thus numerical values located in the bottom left-hand side of a field indicate high intensities and numerical values located in the top right-hand side indicate low intensities. FIG. 6 shows an image 35 with axes 36 and 37. Values for the area of a fault, for example in CM2, are plotted along the axis 36 and values for the intensity of a fault in percentages along the axis 37. This image 35 is also divided into fields or classes by lines 38 to 43. Symbols which indicate the intensity of the fault through the strength of the color are drawn in at the intersections of the lines 38–43. Numerical values in the fields indicate the number of faults occurring in the class concerned.

Figure 7:
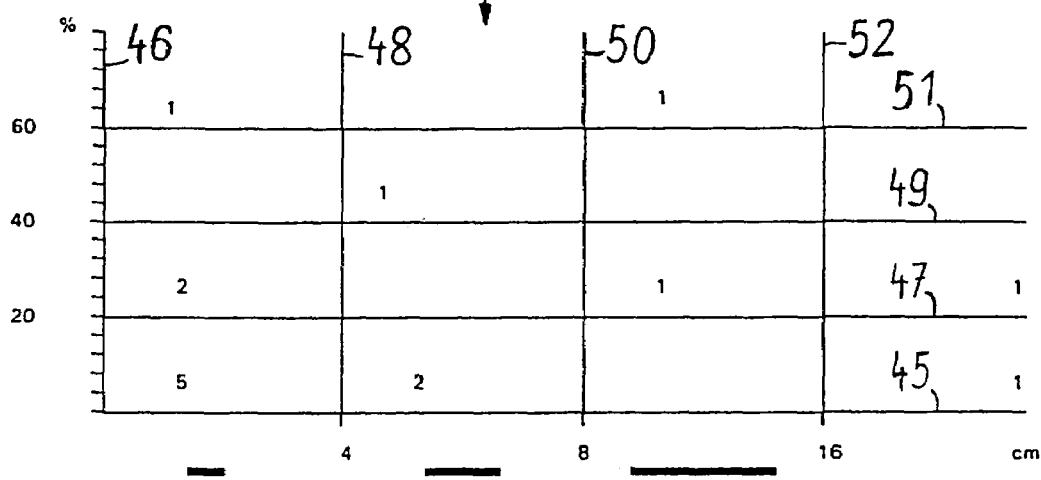
Figure 8:
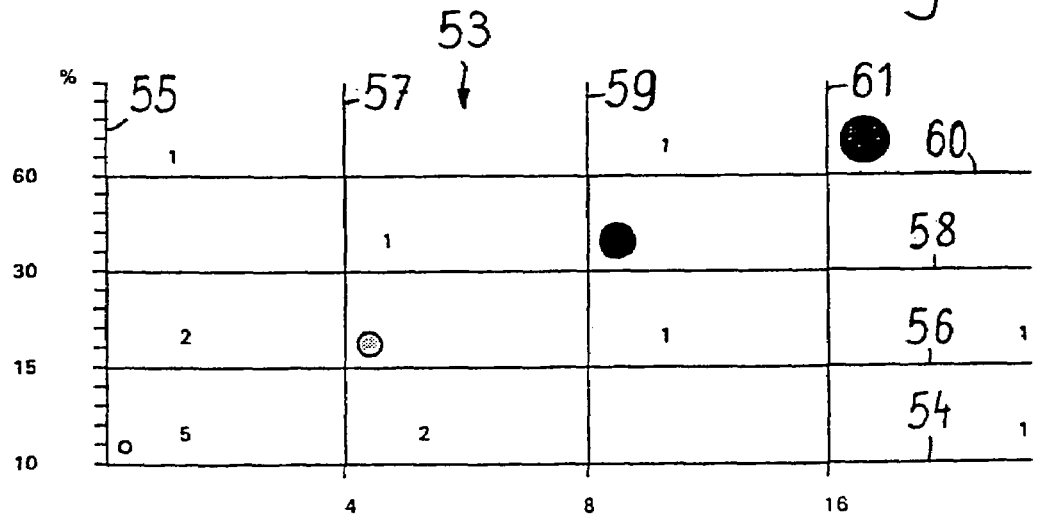

FIG. 7 shows an image 44 with axes 45 and 46. Values for the length of a fault, for example in cm, are plotted along the axis 45 and values for the intensity of a fault, for example in percentages, along the axis 46. This image 44 is also divided into fields or classes by lines 47 to 52. The number of detected faults is indicated by the figures in the fields, as already known from FIG. 3. FIG. 8 shows an image 53 with axes 54 and 55. Values for the number of occupied fields 9 according to FIG. 2 are plotted along the axis 54 and values for the intensity of a fault along the axis 55. This image 53 is also divided into fields or classes by lines 56 to 61. The number of detected faults is indicated by the figures in the fields, as already known for FIG. 3.

Figure 9:
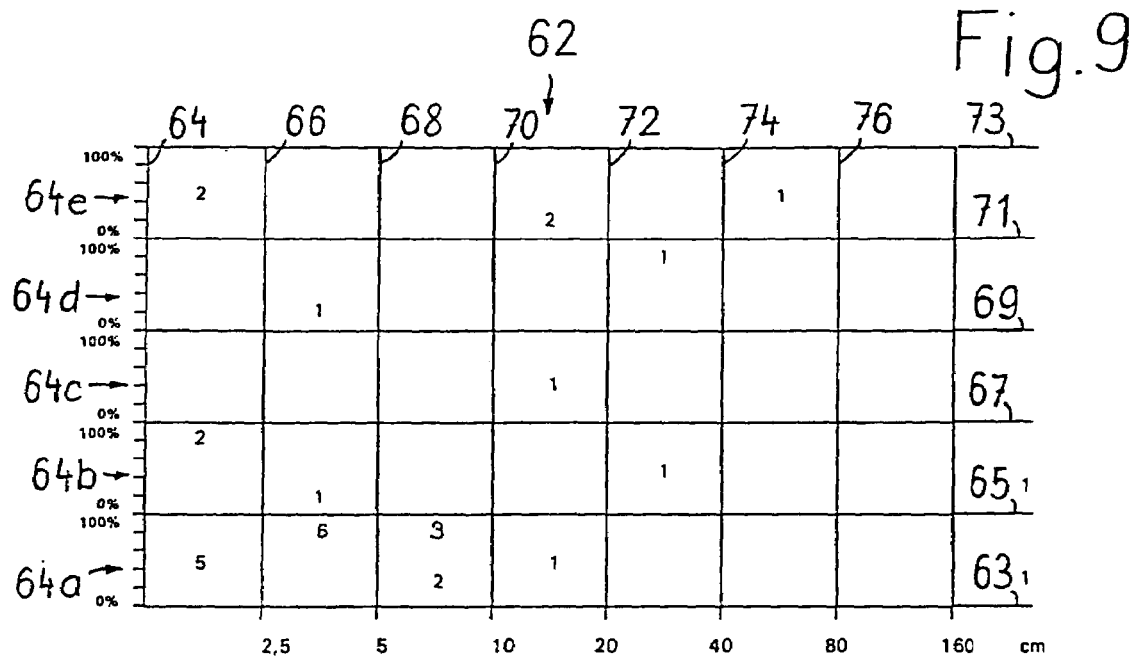

FIG. 9 shows an image 62 with axes 63 and 64. Values for the length of faults in cm are plotted along the axis 63. The axis 64 is divided into a plurality of zones 64a to e, and values for the intensity are given in percentages in each zone. Each of the zones 64a to 64e relates to a certain type of fault, for example the zone 64a relates to weft faults, the zone 64b to warp faults, the zone 64c to surface faults, the zone 64d to edge faults and the zone 64e to holes. Lines 65 to 76 again divide the image 62 into fields or classes in which numerical values indicate the number of detected faults in the class concerned. The position of the numerical value in relation to the zone on the axis 64 indicates the intensity of the fault. Several numerical values may thus also occur in one class. The image 62 thereby illustrates a classification which is based on different types of fault. Different known types of fault may be grouped together as desired. So, for example, the term "weft faults" is here generally understood to mean faults which predominantly extend weftwise in a woven fabric. Such faults are known under the following terms: join, fell, straightening point, shed, weft bar, lashing-in, slubber, fly, thread breakage, mispick.

Figure 10:
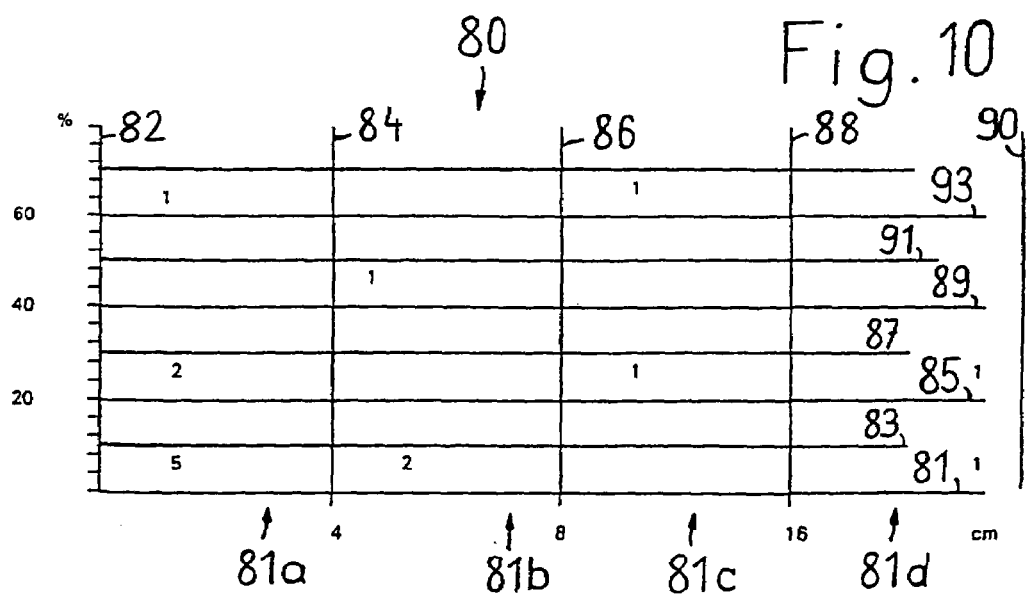

FIG. 10 shows an image 80 with an axis 81 which is divided into zones 81a to d. Values for intensities in percentages are given along another axis 82. Lines 83 to 93 divide the image 80 into fields or classes. Values for the number of detected faults can again be entered in the fields or classes. For example, the intensity of weft faults can be entered in zone 81a, the intensity and size of wrap faults in zone 81b, the intensity or size of holes in zone 81c, the intensity of edge faults, etc. in zone 81d, and the numbers thereof.

FIG. 11 shows an image 94 with axes and lines as already found in images 12 and 30 (FIGS. 3 and 4). Here the fields or classes are divided by a boundary 97 into two groups 95 and 96, with the boundary extending along lines 15, 17, 19 and 16, 18, 20. However it is also possible to define a boundary 98 which also divides the individual fields or classes.

The method according to the invention is carried out as follows: The textile fabric is scanned in a manner known per se, for example by a camera, and images for swatches of the surface of the fabric are made and signals derived therefrom are processed. Using algorithms, which do not constitute the subject matter of this invention, for image processing, faults or unusual features in the images of the surface are determined from the derived signals by comparison with predetermined limit values, patterns, etc. Thus data on faults in a swatch of the fabric are produced. A swatch of this kind is shown, for example, in FIG. 1 and called a run 1. A fault 2, which is distinguished by various parameters, can be recognized in this. These parameters are its position, which is given by coordinates x and y, its size, which is given by the values s and k, and its intensity, which causes the fault to actually stand out from the area surrounding it and which is quantified by a qualitative datum, here called delta i.

Different parameters are significant, according to how the fault is subsequently dealt with. For example, if every fault is to be removed, all that is of interest is its position, possibly also its size. If the fabric is then to be assessed as to where the faults are most numerous, such as at the edge, for example, it is again just the position which is of interest. The data are then sorted according to parameters such as length and width and accordingly represented in an image.

Should there be a requirement for assessing how the fault appears to the eye or how it influences subsequent processing of the fabric, such as dyeing or dressing, its size is of interest and possibly also its intensity. Then the parameters according to which the data are sorted are the length s and the width k of the fault, as well as its intensity delta i.

Just one dimension may be determined from the signals obtained from image processing in order to detect the size of a fault, or an evaluation according to FIG. 2 may be undertaken. In this case an investigation is carried out to establish how many fields 9 are affected or at least partly covered by a fault. These fields, as marked in swatch 3a, are counted for each fault and the number is plotted, for example, along the axis 54 in FIG. 8. However it is also possible, as shown for swatch 3b, to take the fields 9 occupied for each fault and to complete them to an extent such that together they form a rectangle which encompasses the fault. The fields 9 which are comprised in this rectangle then have to be counted and plotted.

In order to detect the intensity of a fault, the color or brightness of the area surrounding the fault is taken as a starting point and an attempt is made to quantify deviations of the color or brightness more or less accurately or in a graduated manner, this being expressed by a value delta i. The devices used for image processing determine the degree to which this is successful.

In order to represent the size of the fault in an image, its length can be detected in the swatch in a manner known per se and represented in an image 12, 30 by a value on the axis 13. The width of the fault can be represented in the same way by a value on the axis 14. Together these two values produce, for example, a dot 33 (FIG. 4). This can be left as a dot or simply treated as a fault in class C2, which would mean that just one counting value would then be increased by one for this class. For this purpose it is possible to specify certain fields or classes as acceptable and others as unacceptable beforehand. The position of the fault in image 13, 30 then immediately reveals how the fault is to be assessed. Should values for faults accumulate in individual classes, this will equally provide an indication for assessing the fabric.

The intensity of a fault can be represented according to the possibilities already presented on the basis of the images 34, 35, 44 and 53 (FIGS. 5–8).

As shown in FIG. 1, swatches of the surface from which the data are acquired which form a rectangle are particularly suitable, for the fabrics in question are also already in the form of rectangles, this being a result of the manufacturing process. Then sides of the swatches should also lie parallel and perpendicularly to the boundaries of the fabric. However the swatch concerned does not conventionally constitute the entire surface of the fabric. This applies to swatches 3a, 3b according to FIG. 2, which is an enlarged view of a part of the run 1 according to FIG. 1.

The form of a fault, as represented by the symbols 23 to 29 in FIG. 3, may also be directly considered as a parameter. In fact a parameter of this kind ultimately consists of two parameters (length and width). However it would also be possible to combine the parameter "form" with the parameter "intensity", as known from FIG. 6, and in this way obtain another combination and therefore another image representation. It thus becomes obvious that only a few possibilities are indicated here, although these can also be developed according to the invention in an obvious manner by combination, for example by interchanging the axes.

Data can be evaluated and, optionally, the textile fabric processed in a differentiated manner, according to whether the determined data belong to groups 95 or 96 (FIG. 11), which are separated by a boundary 97, 98. For example, the weighting of the faults in group 96 may be reduced with respect to the faults in group 95. Or faults of group 96 are only marked, for example, at the edge of a cloth run, while faults of group 95 are removed, for example by unraveling the woven fabric in the area around these faults. Generally speaking, boundaries 97, 98, etc. can form groups of classes or categories of faults which initiate different actions.

What is claimed is:

1. A method for representing faults detected on textile fabrics for purposes of evaluation, comprising the following steps:
   receiving data associated with a plurality of faults detected on a swatch of the surface of the fabric;
   sorting the data associated with the plurality of detected faults in accordance with at least two parameters, wherein at least one of said two parameters pertains to the size of the detected faults;
   representing the received and sorted data associated with the plurality of detected faults in an image having at least two dimensions, wherein one of said dimensions corresponds to said one of said two parameters, and another of said dimensions corresponds to the other of said two parameters.

2. The method of claim 1, wherein said one parameter is the length of a detected fault.

3. The method of claim 2 wherein the other of said two parameters is the intensity of a detected fault.

4. The method of claim 2 wherein the other of said two parameters is the width of a detected fault.

5. The method of claim 1 wherein said one parameter is the area of a detected fault.

6. The method of claim 5 wherein the other of said two parameters is the intensity of a detected fault.

7. The method of claim 1 wherein said one parameter is the number of unit fields in said swatch within which a detected fault is located.

8. The method of claim 7 wherein the other of said two parameters is the intensity of a detected fault.

9. The method of claim 1 wherein said other dimension is divided into a plurality of zones that are respectively associated with different types of faults.

10. The method of claim 1 wherein each of said two dimensions is divided into a plurality of sections to thereby divide said image into a plurality of classes, and the plurality of detected faults are represented as numerical values within the classes with which they are respectively associated.

11. The method of claim 10 wherein the position of a numerical value within a class indicates the value of a parameter for detected faults represented by that number.

12. The method of claim 11 wherein the parameter depicted by the positions of the numerical values is a third parameter different from said two parameters.

13. The method of claim 12 wherein said third parameter is intensity.

14. A method for representing faults detected on textile fabrics for purposes of evaluation, comprising the following steps:
   receiving data associated with a plurality of faults detected on a swatch of the surface of the fabric;
   sorting the data associated with the plurality of detected faults in accordance with at least two parameters, wherein at least one of said two parameters pertains to the intensity of the detected faults;
   representing the received and sorted data associated with the plurality of detected faults in an image having at least two dimensions, wherein one of said dimensions corresponds to said one of said two parameters, and another of said dimensions corresponds to the other of said two parameters.

15. The method of claim 14 wherein one of said dimensions is divided into a plurality of zones that are respectively associated with different types of faults.

16. The method of claim 14 wherein each of said two dimensions is divided into a plurality of sections to thereby divide said image into a plurality of classes, and the plurality of detected faults are represented as numerical values within the classes with which they are respectively associated.

17. The method of claim 16 wherein the position of a numerical value within a class indicates the value of a parameter for detected faults represented by that number.

* * * * *